United States Patent [19]

Schmidt et al.

[11]  4,170,587

[45]  Oct. 9, 1979

[54] STATISTICAL MIXTURES OF HALOGENATED BISPHENOLS WITH HALOGEN-FREE BISPHENOLS, A PROCESS FOR THEIR PREPARATION AND THEIR USE FOR THE PREPARATION OF HIGH-MOLECULAR WEIGHT THERMOPLASTIC POLYCARBONATES

[75] Inventors: Manfred Schmidt; Dieter Freitag; Werner Nouvertné, all of Krefeld, Fed. Rep. of Germany

[73] Assignee: Bayer Aktiengesellschaft, Leverkusen, Fed. Rep. of Germany

[21] Appl. No.: 849,278

[22] Filed: Nov. 7, 1977

Related U.S. Application Data

[62] Division of Ser. No. 678,807, Apr. 21, 1976, Pat. No. 4,075,119.

[30] Foreign Application Priority Data

May 7, 1975 [DE] Fed. Rep. of Germany ....... 2520316
May 7, 1975 [DE] Fed. Rep. of Germany ....... 2520317
Dec. 17, 1975 [DE] Fed. Rep. of Germany ....... 2556739

[51] Int. Cl.$^2$ .......................... C08L 69/00; C08K 7/14
[52] U.S. Cl. ................................ 260/37 PC; 252/182; 525/433; 260/DIG. 24; 528/171; 528/202
[58] Field of Search ............. 260/47 XA, 860, 37 PC, 260/49; 252/182, 188.3 R

[56]  References Cited

U.S. PATENT DOCUMENTS

| | | | |
|---|---|---|---|
| 3,231,603 | 1/1966 | Hennis et al. | 260/619 A |
| 3,363,007 | 1/1968 | Majewski et al. | 260/619 A |
| 3,437,637 | 4/1969 | Matzner et al. | 260/47 XA |
| 3,575,927 | 4/1971 | Jackson, Jr. et al. | 260/47 |
| 3,897,392 | 7/1975 | Haupt et al. | 260/47 XA |
| 3,897,394 | 7/1975 | Moore | 260/47 R |
| 3,920,573 | 11/1975 | Vegter et al. | 252/182 |
| 3,965,064 | 6/1976 | Mercier et al. | 260/47 XA |

OTHER PUBLICATIONS

Chemical Abstract No. 20082w, Wielgosz 7/24/1972 vol. 77, #4, p. 5.

Primary Examiner—Theodore E. Pertilla
Attorney, Agent, or Firm—Gene Harsh; Lawrence S. Pope

[57]  ABSTRACT

The invention relates to statistical mixtures of halogenated bisphenols with halogen-free bisphenols and to processes for their preparation. This invention further relates to new aromatic, bromine-containing and/or chlorine-containing, high-molecular weight thermoplastic polycarbonates with good resistance to fire (oxygen index $\geq 36\%$) and good flow properties, to their preparation from the statistical mixtures of halogenated bisphenols and halogen-free bisphenols and to their use alone or as a mixture with halogen-free polycarbonates or with thermoplastic polyesters for the preparation of moldings, films and fibers.

18 Claims, No Drawings

STATISTICAL MIXTURES OF HALOGENATED BISPHENOLS WITH HALOGEN-FREE BISPHENOLS, A PROCESS FOR THEIR PREPARATION AND THEIR USE FOR THE PREPARATION OF HIGH-MOLECULAR WEIGHT THERMOPLASTIC POLYCARBONATES

This is a division of application Ser. No. 678,807 filed Apr. 21, 1976, now U.S. Pat. No. 4,075,119.

BACKGROUND OF THE INVENTION

Flame-resistant polycarbonates have in the past been prepared industrially preferably by the incorporation of tetrahalogenated dihydric phenols, for example of tetrachlorobisphenol A or tetrabromobisphenol A. Although grading in a category of high flame resistance (for example v-o according to Underwriters' Laboratories, Subj. 94) can be achieved in this way, this process effects a drastic impairment in the processability of the corresponding polycarbonates, which is caused by the reduced flow properties and reduced heat stability of these polycarbonates.

Polycarbonates can also be rendered flameproof by admixing homopolycarbonates or copolycarbonates based on halogenated bisphenols, but this process also does not give molding compositions which have good processability combined with good flame-resistance.

Mixtures of an aromatic homopolycarbonate with a low-molecular weight homopolycarbonate obtained from tetrahalogenated bisphenols, such as, for example, tetrabromobisphenol A, are also known. Products of this type also display greatly reduced flowability and reduced heat stability, which have an adverse effect on their behaviour or processing in injection molding machines (for literature, see, for example U.S. Pat. No. 3,334,154 and DT-OS (German Published Specification) No. 2,243,226).

Even compared with the halogenated polycarbonates according to DT-OS (German Published Specification) No. 2,315,888 and U.S. Pat. No. 3,912,687, incorporated herein by reference, and their admixtures with other polycarbonates, for example bisphenol A polycarbonates, the polycarbonates according to the present invention show improved intrinsic viscous properties associated with equal or better flame-resistance.

Thus, to summarize it can be stated that customary halogen-containing polycarbonates themselves, and their admixtures with halogen-free polycarbonates, certainly show improved behaviour in burning, but have processing disadvantages due to the reduced flowability.

BRIEF SUMMARY OF THE INVENTION

The invention relates to statistical mixtures of halogenated bisphenols of the formula I and halogen-free bisphenols of the formula II and to processes for their preparation. This invention further relates to new aromatic, bromine-containing and/or chlorine-containing high molecular weight thermoplastic polycarbonates with good resistance to fire (oxygen index $\geq 36\%$) and good flow properties, to their preparation from the statistical mixtures of halogenated bisphenols of the formula I and halogen-free bisphenols of the formula II, and to their use alone or as a mixture with halogen-free polycarbonates or with thermoplastic polyesters for the preparation of moldings, films and fibers.

Surprisingly, it has now been found that polycarbonates with a surprisingly advantageous spectrum of properties are obtained from statistical mixtures of halogenated bisphenols of the formula I with non-halogenated bisphenols of the formula II. These bromine-containing and/or chlorine-containing polycarbonates according to the invention are distinguished, on the one hand, by their outstanding flow properties, which give rise to their good processing properties. On the other hand, the polycarbonates according to the invention possess an even better fire-resistance (oxygen index $\geq 36\%$) than, for example, those polycarbonates which contain the same amounts by weight of halogen due to incorporation of pure tetrahalogenated bisphenols or which contain the same amounts by weight of halogen due to mixing in for example, a low-molecular weight tetrahalogenobisphenol homopolycarbonate.

The new aromatic, high-molecular weight thermoplastic polycarbonates according to the invention have a total halogen content of about 2–45% by weight, preferably about 3–27% by weight. The following applies with regard to the total halogen content; the polycarbonate can contain bromine alone in amounts by weight of about 0–45%, chlorine alone in amounts by weight of about 0–27%, or chlorine and bromine conjointly in any desired ratios by weight.

DETAILED DESCRIPTION OF THE INVENTION

The statistical mixtures which are suitable for the preparation of the polycarbonates of the invention are statistical mixtures comprising halogen-free bisphenols of the formula II with mono-, di-, tri- and tetrahalogenated bisphenols, wherein the halogen is selected from the group consisting of bromine and chlorine, of the formula I

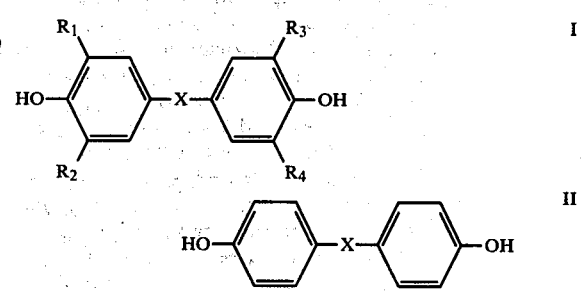

wherein
X denotes $C_1$–$C_9$ alkylene, $C_2$–$C_9$ alkylidene, $C_5$–$C_{15}$ cycloalkylene, $C_5$–$C_{15}$ cycloalkylidene, a single bond, —O—, —S—, —SO—, —SO$_2$—, —CO— or

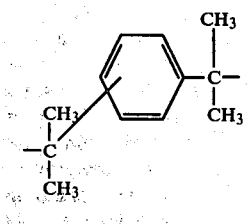

and
$R_1$ to $R_4$ are identical or different and denote H, Br and Cl and at least one R is Br or Cl.

Statistical mixtures are understood to mean mixtures of reaction products and, in some cases, corresponding starting materials, such as are customarily formed in chemical reactions, for example in halogenation reactions, which are obtained if the reaction between the reactants does not produce one reaction product.

In the applicants' process of halogenating bisphenols, four hydrogen atoms can be replaced by bromine or chlorine. However, in any halogenation reaction, mixtures of non-, mono-, di-, tri- and tetrahalogenated bisphenols in amounts corresponding to the statistical Gaussian distribution are obtained. Accordingly, if each mol of bisphenol were halogenated with one mole of $Br_2$, the reaction product would consist of a statistical mixture of non-, mono-, di-, tri- and tetrabrominated bisphenol; or if each mol of bisphenol were halogenated with four mols of $Br_2$, the reaction product would consist of a statistical mixture of non-, mono-, di-, tri- and tetrabrominated bisphenol.

A characteristic of the mixtures of bisphenols which are suitable according to the invention is that they are composed of mono-, di-, tri- and tetrahalogenated bisphenols and non-halogenated bisphenols with a total halogen content of about 3–48% by weight, preferably about 4–30% by weight, and that the statistical mixtures which are suitable according to the invention can contain bromine alone in amounts by weight of about 0–48% by weight, chlorine alone in amounts by weight of about 0–30% by weight, or bromine and chlorine conjointly in any desired ratios by weight.

These statistical mixtures can be prepared, for example, by partial bromination and/or chlorination of bisphenols of the formula II. This can be carried out in an organic suspension agent suitable for bisphenols. A suitable process is also the partial bromination and/or chlorination of bisphenols of the formula II in a gas/solid phase reaction. The statistical mixture of bisphenols obtainable by these halogenation processes can be used directly for the preparation of polycarbonates. In these bromination and/or chlorination reactions, in suspension or in a gas/solid phase reaction, the bisphenols of the formula II are reacted with the amounts of bromine and/or chlorine required in a particular case by the bromine and/or chlorine content of the mixtures to be prepared; these amounts of bromine, which are required for bromination only, are calculated from the desired amount by weight of bromine in the end product and 10% by weight of this amount is added to account for losses during the reaction; in the case of the gas/solid phase halogenation process, this proportion lost is increased to 20% by weight and must be included in the calculations at the start of the reaction. The losses of bromine due to the formation of HBr are not substantial since the HBr formed is reactivated again by the addition of chlorine, BrCl being formed.

The ratios of the reactants for chlorination only are to be calculated quantitatively as a function of the chlorine content of the end product for the suspension process and 10% by weight is to be taken into account for losses during the reaction; for the gas/solid phase chlorination, a chlorine loss of at least 20% by weight must be taken into account. For both chlorination methods, in suspension or in a gas/solid phase reaction, the loss due to the formation of HCl, in the sense of the course of the reaction, must also be taken into account.

The amounts of chlorine and bromine required for the preparation of the chlorine-containing and bromine-containing mixtures of bisphenols correspond to the calculated amounts by weight in the desired end product as well as an additional amount of 10% of the calculated amount of chlorine and bromine which is to be included due to the reacton losses in the case of the suspension process. In the case of the gas/solid phase halogenation process, the extra amounts of bromine and chlorine required due to losses is increased by at least 20% of the calculated amount of bromine and chlorine.

Bisphenols of the formula II which are suitable for the halogenation are: bis-(hydroxyphenyl)-alkanes, bis-(hydroxyphenyl)-cycloalkanes, bis-(hydroxyphenyl) sulphides, bis-(hydroxyphenyl) ethers, bis-(hydroxyphenyl) ketones, bis-(hydroxyphenyl)-sulphones and $\alpha,\alpha'$-bis-(hydroxyphenyl)-diisopropylbenzenes.

Bisphenols of this type are described, for example, in U.S. Pat. Nos. 3,028,365, 2,999,835, 3,148,172, 3,271,368, 2,991,273, 3,271,367, 3,280,078, 3,014,891 and 2,999,846 all incorporated herein by reference, and in German Published Specifications Nos. 1,570,703, 2,063,050, 2,063,052, 2,211,956 and 2,211,957, in French Pat. Specification No. 1,561,518 and in the monograph "H. Schnell, Chemistry and Physics of Polycarbonates, Interscience Publishers, New York, 1964".

Examples of preferred bisphenols are: 2,2-bis-(4-hydroxyphenyl)-propane, 2,4-bis-(4-hydroxyphenyl)-2-methylbutane, 1,1-bis-(4-hydroxyphenyl)-cyclohexane and $\alpha,\alpha'$-bis-(4-hydroxyphenyl)-p-diisopropylbenzene.

Examples of particularly preferred bisphenols are: 2,2-bis-(4-hydroxyphenyl)-propane (bisphenol A) and 1,1-bis-(4-hydroxyphenyl)-cyclohexane (bisphenol Z).

When the statistical mixtures of bisphenols are prepared by the gas/solid phase halogenation process, the bisphenols of the general formula II, which are to be halogenated, are brought into contact, in the flaked or ground form (average particle size 300–600μ) with a constant stream of chlorine gas and/or with a stream of inert gas, consisting of nitrogen or carbon dioxide, which is charged with bromine vapors. The rate of flow of the gaseous halogens and thus the amounts of halogen fed to the reaction per unit time, depend on the amount of the bisphenols to be halogenated and on the desired total halogen content in the product and in general is preferably about 0.1–3.0 mols of halogen per mole of bisphenol and per hour, most preferably about 1–2 mols of halogen per mol of bisphenol and per hour. The reaction is carried out in the course of 5–120 minutes, preferably in the course of 10–60 minutes. The reaction temperature should be between about −20° C. and 89° C., but preferably between about +10° C. and +40° C.

A variable in the gas/solid phase halogenation process is the choice of the reaction vessel or the reaction space; however, attention must be paid to ensuring that there is a possibility for good contact between the bisphenol and the halogen. The powdered bisphenol can be reacted in a flask with the gaseous halogen or mixture of halogens, homogeneous mixing being provided by stirring. It is also possible to feed the ground bisphenol, in a thin 0.1–2 cm layer on a conveyor belt, continuously through a reaction space in which it is brought into contact with bromine and/or chlorine in the above mentioned concentration ratios of halogen per bisphenol and per hour. The halogen content to be produced in the bisphenol is a function of the contact time and thus of the time of reaction between the bisphenol and the halogen, the relationship being such that the halogen content of the bisphenol mixtures which are suitable according to the invention is directly proportional to the time of contact between the bisphenol and the halogen. Thus, the contact time and, accordingly, the halogen content of the statistical mixtures according to the invention can be regulated in a simple manner by the speed of a conveyor belt which feeds the bisphenol through the reaction space. The preparation of the statistical mixtures of bisphenols by the gas/solid phase halogenation process can also be carried out by the fluidization method in a fluidized bed. In this case the bisphenol to be halogenated is reacted, as granular material which can be fluidized, with the gaseous halogens in the counter current flow.

In their various embodiments, these gas/solid phase halogenation processes are distinguished by the advantageous absence of a solvent or suspension medium, due to which involved operations to separate or purify the statistical mixtures of bisphenols, which are suitable according to the invention, are dispensed with and these mixtures can thus be directly reacted to give high-molecular weight polycondensation products.

Thus, the present invention also relates to a process for the preparation of the statistical mixtures of halogenated bisphenols of the formula I and halogen-free bisphenols of the formula II, which is characterized in that the bisphenols of the formula II are brought into contact, in the solid form at temperatures between about $-20°$ C. and $+80°$ C., preferably between about $+10°$ C. and $+40°$ C., with gaseous chlorine and/or bromine, optionally also using an inert gas, preferably in amounts of about 0.1-3 mols of halogen per mol of bisphenol and per hour, and the resulting statistical mixture of halogenated bisphenols of the formula I and bisphenols of the formula II is withdrawn from the further reaction after the desired halogen content has been reached.

For the preparation of the statistical mixtures of bisphenols by partial halogenation of the bisphenols of the formula II in suspension, the bisphenols are suspended, for example in amounts of 2 kg, in about 2 to 5 times the amount by weight of a halogen-containing hydrocarbon, such as carbon tetrachloride. The amounts of bromine and/or chlorine required for the desired halogen content are introduced in the course of 2-60 minutes while cooling. The reaction temperature can be from about $-20°$ C. to $+80°$ C., but preferably about $+10°$ C. to $50°$ C. Chlorination only of the bisphenol is carried out only with chlorine gas. If the bisphenol is to be brominated only by passing in bromine and chlorine, the supply of chlorine gas must be so adjusted at the start of the bromine addition that no chlorination of the bisphenol occurs but the hydrobromic acid which forms reacts exclusively according to the equation (1) formulated below with chlorine to give bromine chloride, which in turn acts as a very reactive brominating agent.

$$HBr + Cl_2 \rightarrow BrCl + HCl \qquad (1)$$

The end of the bromination reaction is clearly recognizable by the disappearance of the bromine coloration; an increase in the amount of chlorine gas introduced during the addition of bromine has, within certain limits (which are also determined by the dimensions of the apparatus) an accelerating effect on the reaction. If chlorine gas is supplied in excess, chlorination of the bisphenol also occurs in competition with the bromination. This also occurs when chlorine is passed into the suspension before or after the addition of bromine. Very diverse bromine and/or chlorine contents in the mixtures of bisphenols can thus be obtained in a simple manner.

After removal of the residual hydrochloric acid gases by flushing with an inert gas, such as nitrogen or carbon dioxide, the statistical mixture of bisphenols, which are suitable according to the invention, can be separated off simply by filtration. If the statistical mixture of bisphenols is dissolved directly in alkali metal hydroxide solutions and the solution is separated off from the suspension medium, the bisphenolate solution can be used directly, without further purification steps, for various subsequent polycondensation reactions.

Thus, the present invention also relates to a process for the preparation of the statistical mixtures, according to the invention, of halogenated bisphenols of the formula I and halogen-free bisphenols of the formula II, which is characterized in that bisphenols of the formula II are suspended in about 2 to 5 times their amount by weight of a halogen-containing hydrocarbon and reacted, at temperatures between about $-20°$ C. and $+80°$ C., with the stoichiometric amounts of bromine and/or chlorine required for the desired halogen content in the mixture of bisphenols.

Other suitable halogenated hydrocarbons, apart from carbon tetrachloride, which is suitable for the halogenation in suspension are, inter alia, also tetrachloroethanes.

In order to achieve the desired halogen content in the mixture of bisphenols, the amounts of bromine and/or chlorine which are required, depending on the type and the amount, are as a rule to be employed in stoichiometric amounts and customary losses of bromine, but especially of chlorine, by diffusion and the like are to be taken into account.

The statistical mixtures, according to the invention, of halogenated bisphenols of the formula I and halogen-free bisphenols of the formula II are outstandingly suitable directly, without any purification, for the preparation of high-molecular weight, flame-resistant polycondensation products, such as polyesters, polyepoxides and polyurethanes, but especially for the preparation of high-molecular weight thermoplastic polycarbonates with an advantageous combination of properties hitherto unknown. Thus, the properties of polycarbonates prepared according to customary processes from the statistical mixtures of bisphenols are, as mentioned above, far superior to those of polycarbonates or mixtures of polycarbonates which have the same total halogen content and have been rendered flame-resistant and which can be obtained, for example, by co-condensation of dibromo- or tetrabromo- or dichloro- or tetrachloro-bisphenol A with bisphenol A or in which the halogen is set to the same amount by weight by admixing a low-molecular tetrahalogenobisphenol homopolycarbonate to a bisphenol A homopolycarbonate.

The polycarbonates prepared from the mixtures, according to the invention, of bisphenols and distinguished by an extremely high flame resistance ($O_2$ index $\geq 36\%$) and a surprisingly advantageous relationship, which was not hitherto known and which is valuable for processing in injection molding machines, between the solution viscosity ($\eta$rel, measured according to DIN 7744) and the melt viscosity (measured in accordance with ASTM-D1703) which gives rise to extremely favorable flow properties. A polycarbonate containing 5% by weight of bromine and 1.2% by weight of chlorine, which was prepared from a bisphenol mixture according to the invention, possesses, for example, an O₂ index of 39%, a relative solution viscosity of $\eta_{rel}=1.333$ (measured in a 0.5% strength by weight solution in methylene chloride at 20° C.) and a melt viscosity (at T=300° C., the rate of deformation D=10³.sec⁻¹), which is equal to that of a non-halogenated bisphenol A polycarbonate with a relative solution viscosity of $\eta_{rel}=1.260$.

In principle, the preparation of the bromine-containing and/or chlorine-containing aromatic thermoplatic polycarbonates according to the invention can be carried out according to all known processes for the preparation of high-molecular weight polycarbonates, according to the known phase boundary process, according to the melt transesterification process and also according to the process in homogeneous phase, that is to say using organic bases and, if appropriate, inert solvents, as described in U.S. Pat. Nos. 3,028,365; 2,999,835; 3,148,172; 3,271,368; 2,991,273; 3,271,367; 3,280,078; 3,014,891 and 2,999,846, all incorporated herein by reference.

When the bromine-containing and/or chlorine-containing aromatic polycarbonates according to the invention are prepared in a known manner according to the phase boundary polycondensation process, the procedure is such that phosgene is passed into the well-stirred 2-phase mixture of the aqueous-alkaline solution of the mixture of bisphenolate to be used according to the invention and a solvent for polycarbonates, a chain stopper being added. The mass of aqueous phase per mol of bisphenolate is about 3 kg; the amount of solvent per kg of polycarbonate is about 11 liters. Examples of solvents for polycarbonates which can be used are methylene chloride, tetrachloroethane, chlorobenzene, chloroform or 1,2-dichloroethane.

The pH value of the reaction solution should be between 12 and 14, preferably pH 13.

The amount of NaOH, relative to the amount of bisphenol employed, should be approximately between 5 and 7 mols of NaOH per mol of bisphenol.

The amount of phosgene, relative to the amount of bisphenol employed, should be about 1.2–2.0 mols of phosgene per mol of bisphenol.

In order to accelerate the reaction and to obtain high-molecular weight products, the addition of customary catalysts, such as tertiary amines or quaternary ammonium compounds or, for certain purposes, also arsonium compounds (compare German Pat. Specification No. 1,046,311), after the phosgenation is recommended. The catalyst concentration is about 2–20 mol %, relative to the amount of bisphenol employed. Examples of catalysts which can be used are triethylamine, tributylamine or dimethylbenzylamine. Suitable chain stoppers are monophenols, such as, for example, phenol, p-tert.-butylphenol, 2,4,6-tribromophenol and pentabromophenol; they are used in customary amounts, preferably in amounts of 2–3 mol %, relative to the amount of bisphenol employed.

The polycarbonates can also be branched by the addition of small amounts of polyhydroxy compound having more than two phenolic OH groups, for example about 0.05–2.0 mol-% (relative to the bisphenols employed). Polycarbonates of this type are described, for example, in German Published Specifications Nos. 1,570,533, 1,595,762, 2,116,974 and 2,113,347, British Patent Specification No. 1,079,821 and in U.S. Pat. No. 3,544,514 incorporated herein by reference. Some of the polyhydroxy compounds which can be used are, for example, phoroglucinol, 4,6-dimethyl-2,4,6-tri-(4-hydroxyphenyl)-hept-2-ene, 4,6-dimethyl-2,4,6-tri-(4-hydroxyphenyl)-heptane, 1,3,5-tri-(4-hydroxyphenyl)-benzene, 1,1,1-tri-(4-hydroxy-phenyl)-ethane, tri-(4-hydroxyphenyl)-phenylmethane, 2,2-bis-[4,4-(4,4'-dihydroxydiphenyl)-cyclohexyl]-propane, 2,4-bis-(4-hydroxyphenyl-4-isopropylphenyl)-phenol, 2,6-bis-(2'-hydroxy-5'-methylbenzyl)-4-methyl-phenol, 2-(4-hydroxyphenyl)-2-(2,4-dihydroxyphenyl)-propane and 1,4-bis-(4',4''-dihydroxytriphenyl-methyl)-benzene.

The "amount of bisphenol employed", used above as a reference quantity, relates to the statistical mixture of bisphenols obtained taking into account the bromine and/or chlorine content, amounts of any by-products which may be present being included as bisphenols or an amount of bisphenols employed.

The reaction temperature for the phase boundary polycondensation can be selected freely within wide limits. Advantageously, the reaction is carried out at temperatures below the boiling points of the solvents, temperatures of from about 0° C. to 30° C., preferably about 15° C. to 27° C. generally being selected as far as possible.

The statistical mixtures of bisphenols of the formulae I and II can also be reacted with diphenyl carbonate by the melt condensation process, in a known manner, to give the high-molecular weight polycarbonates according to the invention.

In general, the polycarbonates according to the invention have average molecular weight (number-average) $\overline{M}_n$ of about 10,000 to 200,000 and above, preferably from about 17,000 to 80,000, which can be determined by the osmometric method.

Thus, the polycarbonates according to the invention have recurrent but not identical structural units of the following formula III

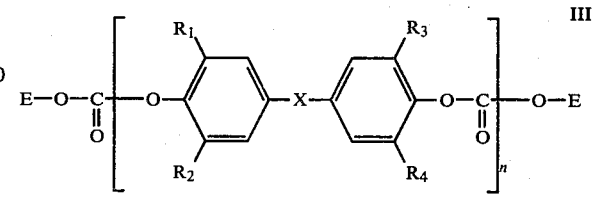

wherein

X denotes $C_1$–$C_9$ alkylene, $C_2$–$C_9$ alyklidene, $C_5$–$C_{15}$ Cycloalkylene, $C_5$–$C_{15}$ cycloalkylidene, a single bond, —O—, —S—, —SO—, —SO₂—, —CO— or

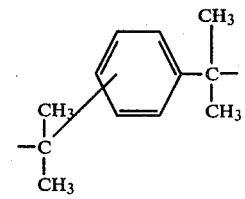

and

R₁ to R₄ are identical or different and denote H, Br or Cl, n is an integer between 20 and 800 and E are the radicals resulting from the chain stoppers, preferably phenyl, $C_1$–$C_6$-alkyl-substituted phenyls or halogen-substituted (bromine-substituted or chlorine-substituted) phenyls, the total halogen content resulting from the individual radicals R₁ to R₄ and E being between about 2% by weight and 45% by weight, preferably between about 3% by weight and 27% by weight.

The halogen-containing polycarbonates according to the invention can be used both as such or as mixtures with halogen-free thermoplastic aromatic polycarbonates and/or thermoplastic polyesters for the preparation of moldings, films and fibers; these moldings, films and fibers have, in addition to the known polycarbonate properties, an improved flame-resistance or non-inflammability and high heat distortion points. However, the excellent processing properties of the halogen-containing polycarbonates according to the invention, which are due to their good flow properties and which distinguish these polycarbonates compared with other polycarbonates with the same halogen content, are to be particularly singled out. Furthermore, the direct flammability of these polycarbonates, measured by the oxygen index text ASTM-D-2,863, is significantly lower than tat of comparison products having the same halogen content (compare table I which follows).

TABLE I

PROCESSING PROPERTIES OF POLYCARBONATES

| Halogen content (% by weight) | | Relative solution viscosity (according to DIN 7,744) | O₂ index (according to ASTM-D-2,863) % | Burning test UL (Subj. 94) 1/16"× ½"× 5" Test Samples | Apparent melt viscosity at 300° C. (according to ASTM-D-1,703) (D=10³ sec⁻¹) |
|---|---|---|---|---|---|
| Bromine | Chlorine | | | | |
| — | — | 1.335 | 27 | 94 v-2 | 800 |
| 5.7ˣ | — | 1.290 | 34 | 94 v-2 | 600 |
| 5.3 | 0.5ˣˣ | 1.309 | 36 | 94 v-0 | 500 |
| — | 11.9ˣˣˣ | 1.286 | 42 | 94 v-0 | 450 |

ˣMixture of tetrabromobisphenol polycarbonate with bisphenol A polycarbonate; This mixture, which has an η rel. of 1.290 and which contains 5.7% by weight of bromine, is prepared analogously to Example 5 of German Published Specification 2,243,226 and specifically is prepared from 100 parts by weight of a high-molecular weight bisphenol A polycarbonate (η rel. 1.300) and 11 parts by weight of the low-molecular weight polycarbonate obtained from 2,2-bis-(3,5-dibromo-4-hydroxyphenyl)-propane with tribromophenoxy end groups, according to Example 1 of German Published Specification 2,243,226.
ˣˣExample 9 of this patent application.
ˣˣˣExample 8 of this patent application.

The polycarbonates according to the invention can also be used readily in mixtures with fillers, for example minerals, wood flour, carbon black, carbon fibers, dyestuffs, pigments, heat stabilizers, UV stabilizers, oxidation stabilizers and other stabilizers, lubricants, plasticisers, mold release agents and other additives.

The compositions, according to the invention, consisting of polycarbonates with a glass fiber content of up to about 40% by weight, relative to the total mixture, are particularly valuable. They can be employed, in particular, where the demand is for extremely high flame-resistance combined with excellent mechanical and electrical properties.

EXAMPLES

EXAMPLE 1

A solution of 1.6 kg of bromine and 1.5 liters of carbon tetrachloride is introduced, in the course of 15 minutes, into a suspension of 2.28 kg of bisphenol A in 3 liters of carbon tetrachloride, while stirring and at an internal temperature of 20°–30° C. At the same time, chlorine is passed in, at a rate of flow of v=100 liters/hour, for a period of 23 minutes until the bisphenol suspension is decolorized, and chlorine gas is then metered in for a further 20 minutes. The mixture is flushed with nitrogen in order to remove the hydrochloric acid gases and the reaction product is filtered off, washed with 1 liter of carbon tetrachloride and dried in vacuo at 30° C. The total halogen content of the mixture of bisphenols is 37.5% by weight, the bromine content being 34% by weight and the chlorine content 3.5% by weight. Chromatographic separation of the mixture gives the following composition: 3.2% by weight of monobromo-bisphenol A, 64.4% by weight of dibromo-bisphenol A, 13.3% by weight of tribromobisphenol A, 14.6% by weight of dichloro-bisphenol A and 4.5% by weight of bisphenol A.

EXAMPLE 2

In a 2 liter vessel, 137 g of powdered 2,2-bis-(4-hydroxy-phenyl)-propane (bisphenol A) (average particle size: 300–600 μ) are brought into contact, while cooling and stirring constantly, with a stream of nitrogen charged with bromine vapors (rate of flow v=10 liters/hour) and at the same time with chlorine gas (rate of flow v=10 liters/hour). After 20 minutes the addition of bromine is ceased and the mixture is further chlorinated for 5 minutes at the same rate of flow. The internal temperature rises from 20° C. to 28° C. In order to remove the hydrochloric acid gases, the reaction vessel is then flushed for ½ hour with nitrogen. The resulting mixture of statistically nuclear-halogenated bisphenol A derivatives with non-halogenated bisphenol A contains 3.0% by weight of bromine and 2.0% by weight of chlorine. Gel chromatographic separation of the mixture gives the following composition: 0.4% by weight of dichloro-bisphenol A, 1.2% by weight of trichloro-bisphenol A, 3.64% by weight of tetrachloro-bisphenol A, 0.2% by weight of monobromo-bisphenol A, 1.5% by weight of tribromo-bisphenol A, 4.8% by weight of tetrabromo-bisphenol A and 88.3% by weight of bisphenol A.

A polycarbonate prepared from this mixture of bisphenols by the customary phase boundary process contains 2.7% by weight of bromine as well as 1.9% by weight of chlorine and has an average molecular weight (number-average) of $\overline{M}n$=97,500 at a relative solution viscosity of $\eta_{rel}$=3.494, measured in a 0.5% strength solution of dichloromethane at 20° C.

EXAMPLE 3

Analogously to Example 2, an equal amount of bisphenol A is brought into contact, under the same reaction conditions, with bromine and chlorine gas for 30 minutes; the mixture is then further chlorinated for 7½ minutes. The mixture of bisphenols obtained after flushing with nitrogen has a total halogen content of 7.8% by weight, the bromine content being 4.8% by weight and the chlorine 3.0% by weight.

The following composition of the mixture is determined by gel chromatographic separation: 2.3% by weight of trichlorobisphenol A, 5.8% by weight of tetrachloro-bisphenol A, 0.2% by weight of mono-bromo-bisphenol A, 0.6% by weight of dibromobisphenol A, 2.8% by weight of tribromo-bisphenol A, 5.0% by weight of tetrabromo-bisphenol A and 83.3% by weight of bisphenol A.

A polycarbonate prepared from this mixture by the phase boundary process contains 4.6% by weight of bromine and 2.3% by weight of chlorine and has an average molecular weight (number-average) of $\overline{M}_n=81,000$ at a relative solution viscosity of $\eta_{rel}=2.825$, measured in a 0.5% strength solution of dichloromethane at 20° C.

EXAMPLE 4

In a 2 liter flask with a ground glass joint, 137 g of powdered 2,2-bis-(4-hydroxyphenyl)-propane (bisphenol A) (average particle size: 300–600 μ) are brought into contact, while cooling and stirring constantly, with a stream of nitrogen charged with bromine vapors (rate of flow v=15 liters/hour) and at the same time with chlorine gas (rate of flow v=10 liters/hour). The internal temperature rises from 20° to 28° C. After 40 minutes the introduction of bromine is ceased and the mixture is further chlorinated for 10 minutes at the same rate of flow. The hydrochloric acid gas is then removed by flushing the reaction vessel with nitrogen. The resulting mixture of statistically nuclear-halogenated bisphenol A derivatives with non-halogenated bisphenol A comprises: 0.8% by weight of trichlorobisphenol A, 3.8% by weight of tetrachlorobisphenol A, 8.7% by weight of tetrabromobisphenol A and 86.7% by weight of bisphenol A.

The total halogen content of the mixture is 6.9% by weight, the bromine content being 5.1% by weight and the chlorine content 1.8% by weight.

Without subsequent purification, the mixture is dissolved in 600 g of 20% strength sodium hydroxide solution and 1.2 liters of distilled water, nitrogen continuing to be passed through the reaction mixture. After the addition of 1.5 liters of dichloromethane, 100 g of phosgene are introduced, while cooling and stirring intensively. The internal temperature is 25° C. When the introduction of phosgene is complete, 2.5 g of triethylamine are added and the mixture is further condensed for one hour at pH 13. The highly viscous polycarbonate solution is then washed with water until neutral and salt-free and the polycarbonate is isolated from the washed solution and dried. It contains 4.9% by weight of bromine and 1.7% by weight of chlorine and has an average molecular weight (number-average) of $\overline{M}_n=49,000$ at a relative viscosity of $\eta_{rel}=3.187$, measured in a 0.5% strength solution of dichloromethane at 20° C.

EXAMPLE 5

In a 2 liters flask with a ground glass joint, 137 g of powdered bisphenol A (average particle size: 300–600 μ) is brought into contact, while cooling and stirring constantly, with chlorine gas (rate of flow v=20 liters/hour) for one hour. The internal temperature rises to 28° C. The reaction vessel is then flushed with nitrogen and the mixture is dissolved in 600 g of 20% strength sodium hydroxide solution and 1.2 liters of distilled water, nitrogen continuing to be passed through the solution. Analysis of the mixture, thus obtained, of statistically nuclear-chlorinated bisphenol A derivatives with non-chlorinated bisphenol A gives the following composition: 1.6% by weight of monochlorobisphenol A, 6.8% by weight of dichlorobisphenol A, 11.2% by weight of trichlorobisphenol A, 2.7% by weight of tetrachlorobisphenol A and 87.7% by weight of bisphenol A.

After adding 1.5 liters of dichloromethane, 100 g of phosgene are introduced into the solution of bisphenolates, while cooling and stirring intensively. The internal temperature is 25° C. When the introduction of phosgene is complete, 2.5 g of triethylamine are added and the mixture is further condensed for one hour at pH 13. The highly viscous polycarbonate solution is then washed with water until neutral and salt-free and the polycarbonate is isolated from the washed solution and dried. It contains 6.3% by weight of chlorine and has an average molecular weight (number-average) of $\overline{M}_n=18,200$ at a relative solution viscosity of $\eta_{rel}=1.316$, measured in a 0.5% strength solution of dichloromethane at 20° C.

EXAMPLE 6

45.6 g of bisphenol A are suspended in 200 ml of carbon tetrachloride. Chlorine gas is passed, at a rate of flow of 60 liters/hour, through the suspension for 5 minutes, while stirring constantly and while cooling, and, while continuing to pass in chlorine, a solution of 7 g of bromine in 50 ml carbon tetrachloride is added in the course of 5 minutes. After passing chlorine in for a further 10 minutes, the suspension is flushed with nitrogen for an hour and the resulting mixture of bisphenols is dissolved, without further purification, in 200 g of 20% strength sodium hydroxide solution and in 500 ml of distilled water, nitrogen continuing to be passed through the reaction mixture. The lower carbon tetrachloride phase is separated off, 680 ml of dichloromethane are added to the solution and, while stirring intensively and cooling, 30 g of phosgene are passed in (maximum internal temperature: 25° C.). When the introduction of phosgene is complete, 0.4 g of triethylamine are added and the mixture is further condensed for one hour at pH 13. The polycarbonate obtained after customary working up contains 9.4% by weight of bromine and 15.1% by weight of chlorine and has an average molecular weight (number-average) of $\overline{M}_n=25,300$ at a relative solution viscosity of $\eta_{rel}=1.263$, measured in a 0.5% strength solution of dichloromethane at 20° C.

EXAMPLE 7

A constant stream of chlorine gas (rate of flow v=15 liters/hour) is passed, in the course of 20 minutes, into a suspension of 22.8 g of bisphenol A in 100 ml of carbon tetrachloride, while cooling. In order to eliminate the hydrochloric acid gases, the mixture is then flushed with nitrogen and dissolved directly, without further purification, in 100 g of 20% strength sodium hydroxide solution and 200 ml of distilled water, nitrogen continuing to be passed through the reaction mixture. The carbon tetrachloride phase is not removed. After adding 250 ml of dichloromethane, 20 g of phosgene are introduced, while stirring intensively and while cooling, at such a rate that the internal temperature does not rise above 25° C. When the introduction of phosgene is complete (duration: 20 minutes), 0.3 g of triethylamine are added and the mixture is further condensed for one hour at pH 13. The polycarbonate obtained after customary working up contains 21.7% by weight of chlorine and has an average molecular weight (number-average) of $\overline{M}_n = 29,600$, at a relative solution viscosity of $\eta_{rel} = 1.303$ (measured in a 0.5% strength solution of dichloromethane at 20° C.), and a freezing point of 160° C. The modulus of elasticity determined on a film in a tension test is 2,370 MPa. (measured according to DIN 53,455)

EXAMPLE 8

Chlorine gas is passed, at a rate of flow of v=150 liters/hour, into a suspension of 977 g of bisphenol A in 2 liters of carbon tetrachloride for 30 minutes, while cooling. The mixture is then flushed with nitrogen for one hour. The mixture, thus obtained, of statistically nuclear-chlorinated bisphenol A derivatives with non-chlorinated bisphenol A contains 12.2% by weight of chlorine, and consists of: 3.1% by weight of monochlorobisphenol A, 68.3% by weight of dichlorobisphenol A, 6.6% by weight of trichlorobisphenol A and 22.0% by weight of bisphenol A.

Directly after flushing with nitrogen and after adding 16.1 g of tert.-butylphenol, the mixture is dissolved in 3.5 kg of 20% strength sodium hydroxide solution and 8.4 liters of distilled water, without discontinuing the introduction of nitrogen. The lower carbon tetrachloride phase is then separated off, 13 liters of dichloromethane are added to the solution and 600 g of phosgene are passed in, while stirring intensively and while cooling (maximum internal temperature 25° C.). When the introduction of phosgene is complete, 12 g of triethylamine are added and the mixture is further condensed for one hour at pH 13. The polycarbonate obtained after customary working up has a chlorine content of 11.9% by weight and an average molecular weight (number-average) of $\overline{M}_n = 19,100$ at a relative solution viscosity of $\eta_{rel} = 1.286$, measured in a 0.5% strength solution of dichloromethane at 20° C.

The oxygen index measured according to ASTM D 2863-70 is 42%. The burning test according to Underwriter's Laboratories (Subj. 94) gives a classification of v−o. The apparent melt viscosity at 300° C. and at a shear rate of $D = 10^3 \sec^{-1}$ is 450 Pa s (Pa s = Pascal × second).

EXAMPLE 9

A solution of 75 g of bromine in 300 ml of carbon tetrachloride is added to a suspension of 977 g of bisphenol A in 3 liters of carbon tetrachloride, while cooling, and, at the same time, a stream of chlorine gas is passed in at a throughput of v=60 liters/hour until the bromine coloration has disappeared (duration: 8 minutes). The mixture is then flushed with nitrogen for one hour in order to eliminate the hydrochloric acid gas. 17 g of tert.-butylphenol are added, and the mixture is dissolved, without purification and while continuing to supply nitrogen, in 3.5 kg of 20% strength sodium hydroxide solution and 8.4 liters of distilled water. Analysis of the statistically nuclear-halogenated bisphenol A mixture gives the following composition: 1.3% by weight of monobromobisphenol A, 2.4% by weight of dichlorobisphenol A, 9.4% by weight of dibromobisphenol A, 2.2% by weight of tribromobisphenol A and 84.7% by weight of bisphenol A.

In order to prepare the polycarbonate, the solution of bisphenolates, thus obtained, is separated off from the lower carbon tetrachloride phase, which can be used for further halogenation reactions. After adding 13 liters of dichloromethane, 600 g of phosgene are passed, at 25° C., into the solution of bisphenolates, while stirring intensively and while cooling. When the introduction of phosgene is complete, 12 g of triethylamine are added and the mixture is further condensed for one hour at pH 13. The polycarbonate obtained after customary working up has a total halogen content of 5.8% by weight, the bromine content being 5.3% by weight and the chlorine content 0.5% by weight. The average molecular weight (number-average) is $\overline{M}_n = 18,200$ at a relative solution viscosity of $\eta_{rel} = 1.309$, measured in a 0.5% strength solution of dichloromethane at 20° C.

The value determined according to ASTM D 2863-70 for the oxygen index is 36%. The burning test according to Underwriter's Laboratories (Subj. 94) gives a classification of v−0. The apparent melt viscosity at 300° C. and at a shear rate of $D = 10^3 \sec^{-1}$ is 500 Pa s.

Although the invention has been described in considerable detail in the foregoing, such detail is solely for the purpose of illustration. Variations may be made by those skilled in the art without departing from the spirit and scope of the invention.

What is claimed is:

1. A composition comprising high-molecular weight, thermoplastic, aromatic polycarbonates containing halogen selected from the group consisting of bromine and chlorine having recurrent but not identical structural units of the following formula III

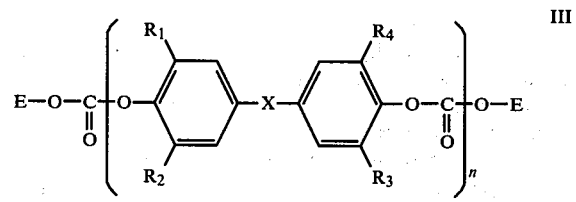

wherein
X denotes $C_1-C_9$ alkylene, $C_2-C_9$ alkylidene, $C_5-C_{15}$ cycloalkylene, $C_5-C_{15}$ cycloalkylidene, a single bond, —O—, —S—, —SO—, —SO$_2$—, —CO— or

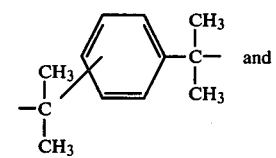

$R_1$ to $R_4$ are identical or different and denote H, Br or Cl,
n is an integer between 20 and 800 and
E are phenyl, $C_1-C_6$-alkyl-substituted phenyl, bromine-substituted phenyl or chlorine-substituted phenyl,
the total halogen content resulting from the individual radicals $R_1$ to $R_4$ and E being between about 2% by weight and 45% by weight, the bromine content being between about 0 and 45% by weight and the chlorine content being between about 0 and 27% by weight wherein said polycarbonates are prepared from statistical mixtures comprising halogen-free bisphenols of the formula II with mono-, di-, tri- and tetrahalogenated bisphenols, wherein the halogen is selected from the group consisting of bromine and chlorine, of the formula I

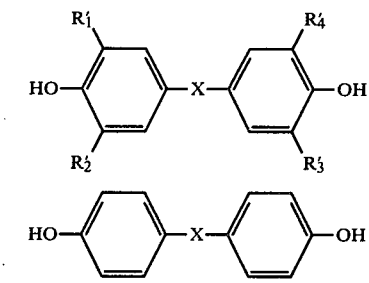

wherein
X denotes $C_1$–$C_9$ alkylene, $C_2$–$C_9$ alkylidene, $C_5$–$C_{15}$ cycloalkylene, $C_5$–$C_{15}$ cycloalkylidene, a single bond, —O—, —S—, —SO—, —SO$_2$—, —CO— or

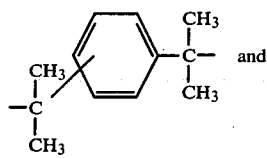

$R_1'$ to $R_4'$ are identical or different and denote H, Br or Cl, and at least one R' is Br or Cl,
wherein the total halogen content of the mixtures is about 3 to 48% by weight and they contain about 0–48% by weight of bromine alone, about 0–30% by weight of chlorine alone or bromine and chlorine conjointly in any desired ratios by weight.

2. A composition comprising high-molecular weight, thermoplastic, aromatic polycarbonates containing halogen selected from the group consisting of bromine and chlorine having recurrent but not identical structural units of the following formula III

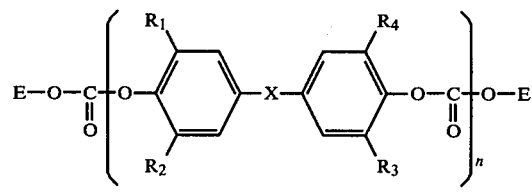

wherein
X denotes $C_1$–$C_9$ alkylene, $C_2$–$C_9$ alkylidene, $C_5$–$C_{15}$ cycloalkylene, $C_5$–$C_{15}$ cycloalkylidene, a single bond, —O—, —S—, —SO$_2$—, —CO— or

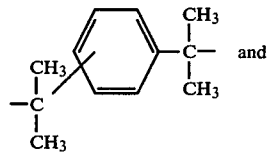

$R_1$ to $R_4$ are identical or different and denote H, Br or Cl,
n is an integer between 20 and 800 and
E are phenyl, $C_1$–$C_6$-alkyl-substituted phenyl, bromine-substituted phenyl or chlorine-substituted phenyl,
the total halogen resulting from the individual radicals $R_1$ to $R_4$ and E being between about 2% by weight and 45% by weight, the bromine content being between about 0 and 45% by weight and the chlorine content being between about 0 and 27% by weight wherein said polycarbonates are prepared from statistical mixtures comprising halogen-free bisphenols of the formula II with mono-, di-, tri- and tetra-halogenated bisphenols, wherein the halogen is selected from the group consisting of bromine and chlorine, of the formula I

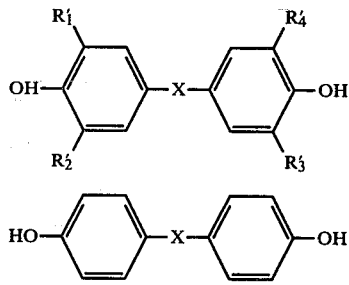

wherein
X denotes $C_1$–$C_9$ alkylene, $C_2$–$C_9$ alkylidene, $C_5$–$C_{15}$ cycloalkylene, $C_5$–$C_{15}$ cycloalkylidene, a single bond, —O—, —S—, —SO—, —SO$_2$—, —CO— or

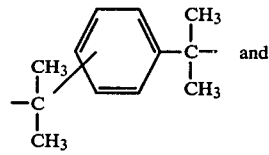

$R_1'$ to $R_4'$ are identical or different and denote H, Br or Cl and at least one R' is Br or Cl,
characterized in that said statistical mixtures have a total halogen content of about 3 to 48% by weight and contain about 0–48% by weight of bromine alone, about 0–30% by weight of chlorine alone or bromine and chlorine conjointly in any desired ratios by weight and wherein said statistical mixtures of bisphenols are prepared by a process comprising bringng bisphenols of formula II in the solid form into contact at temperatures between about −20° C. and +80° C., with gaseous chlorine, bromine, or chlorine and bromine optionally using an inert gas, and subsequently withdrawing the resulting statistical mixture of bisphenols from the further reaction after the desired halogen content has been reached.

3. A composition comprising high-molecular weight, thermoplastic, aromatic polycarbonates containing halogen selected from the group consisting of bromine and chlorine having recurrent but not identical structural units of the following formula III

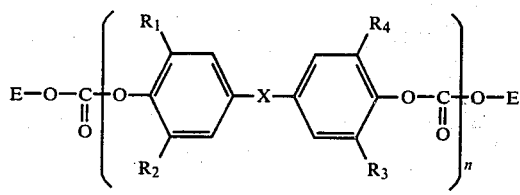  III wherein
X denotes $C_1$–$C_9$ alkylene, $C_2$–$C_9$ alkylidene,
$C_5$–$C_{15}$ cycloalkylene, $C_5$–$C_{15}$ cycloalkylidene
a single bond, —O—, —S—, —SO—, —$SO_2$—,
—CO— or

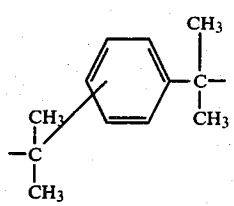

and
$R_1$ to $R_4$ are identical or different and denote H, Br or Cl,
n is an integer between 20 and 800 and
E are phenyl, $C_1$–$C_6$-alkyl-substituted phenyl, bromine-substituted phenyl or chlorine-substituted phenyl,
the total halogen content resulting from the individual radicals $R_1$ to $R_4$ and E being between about 2% by weight and 45% by weight, the bromine content being between about 0 and 45% by weight and the chlorine content being between about 0 and 27% by weight wherein said polycarbonates are prepared from statistical mixtures comprising halogen-free bisphenols of the formula II with mono-, di-, tri- and tetra-halogenated bisphenols, wherein the halogen is selected from the group consisting of bromine and chlorine, of the formula I:

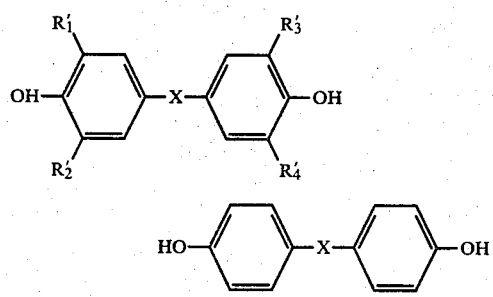

wherein
X denotes $C_1$–$C_9$ alkylene, $C_2$–$C_9$ alkylidene,
$C_5$–$C_{15}$ cycloalkylene, $C_5$–$C_{15}$ cycloalkylidene,
a single bond, —O—, —S—, —SO—, —$SO_2$—,
—CO— or

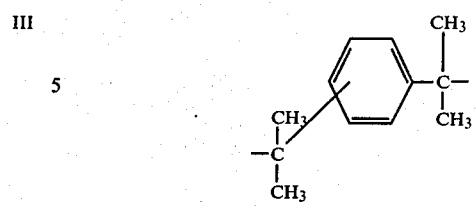

and
$R_1'$ to $R_4'$ are identical or different and denote H, Br or Cl and at least one R' is Br or Cl,
characterized in that said statistical mixtures have a total halogen content of about 3 to 48% by weight and contain about 0–48% by weight of bromine alone, about 0–30% by weight of chlorine alone or bromine and chlorine conjointly in any desired ratios by weight and wherein said statistical mixtures of bisphenols are prepared by a process comprising suspending bisphenols of formula II in about 2 to 5 times the amount by weight of halogen-containing hydrocarbon and reacting, at temperatures between about −20° C. and +80° C., with the amounts of bromine, chlorine, or bromine and chlorine required for the desired halogen content in the mixture of bisphenols.

4. A composition comprising high-molecular weight, thermoplastic, aromatic polycarbonates containing halogen selected from the group consisting of bromine and chlorine having recurrent but not identical structural units of the following formula III

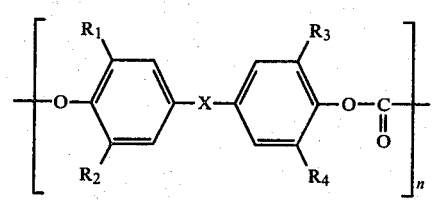  III wherein
X denotes $C_1$–$C_9$ alkylene, $C_2$–$C_9$ alkylidene,
$C_5$–$C_{15}$ cycloalkylene, $C_5$–$C_{15}$ cycloalkylidene,
a single bond,
—O—, —S—, —SO—, —$SO_2$—, —CO— or

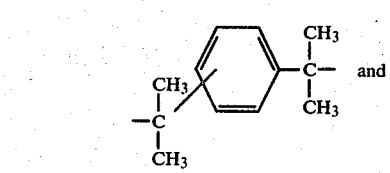 and $R_1$ to $R_4$ are identical or different and denote H, Br or Cl, and n is an integer between 20 and 800, wherein said polycarbonates are prepared from statistical mixtures comprising halogen-free bisphenols of the formula II with mono-, di-, tri- and tetra-halogenated bisphenols, wherein the halogen is selected from the group consisting of bromine and chlorine, of the formula I

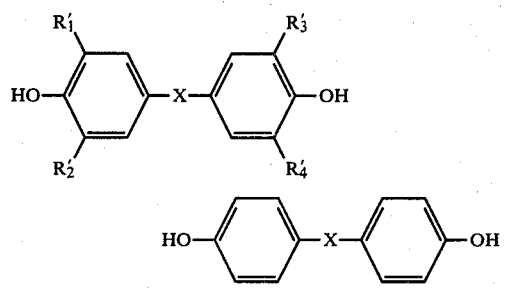

wherein
X denotes C$_1$–C$_9$ alkylene, C$_2$–C$_9$ alkylidene, C$_5$–C$_{15}$ cycloalkylene, C$_5$–C$_{15}$ cycloalkylidene, a single bond, —O—, —S—, —SO—, —SO$_2$—, —CO— or

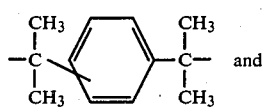 and

R$_1'$ to R$_4'$ are identical or different and denote H, Br or Cl, and at least one R' is Br or Cl,
wherein the total halogen content of the mixtures is about 3 to 48% by weight and they contain about 0–48% by weight of bromine alone, about 0–30% by weight of chlorine alone or bromine and chlorine conjointly in any desired ratios by weight.

5. A composition comprising high-molecular weight, thermoplastic, aromatic polycarbonates containing halogen selected from the group consisting of bromine and chlorine having recurrent but not identical structural units of the following formula III

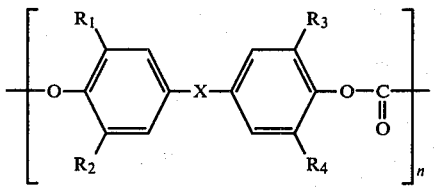

wherein
X denotes C$_1$–C$_9$ alkylene, C$_2$–C$_9$ alkylidene, C$_5$–C$_{15}$ cycloalkylene, C$_5$–C$_{15}$ cycloalkylidene, a single bond,
—O—, —S—, —SO—, —SO$_2$—, —CO— or

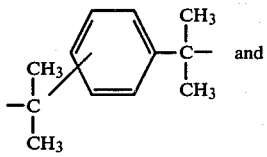 and

R$_1$ to R$_4$ are identical or different and denote H, Br or Cl, and n is an integer between 20 and 800, wherein said polycarbonates are prepared from statistical mixtures comprising halogen-free bisphenols of the formula II with mono-, di-, tri- and tetra-halogenated bisphenols, wherein the halogen is selected from the group consisting of bromine and chlorine, of the formula I

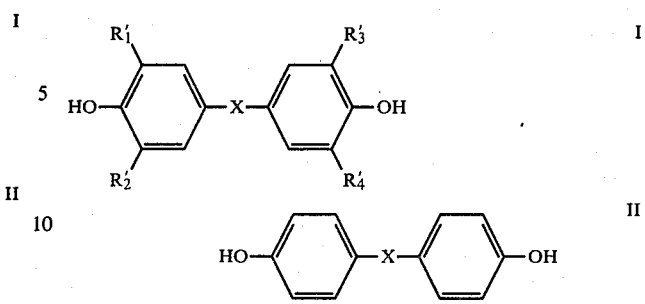

wherein
X denotes C$_1$–C$_9$ alkylene, C$_2$–C$_9$ alkylidene, C$_5$–C$_{15}$ cycloalkylene, C$_5$–C$_{15}$ cycloalkylidene, a single bond, —O—, —S—, —SO—, —SO$_2$—, —CO— or

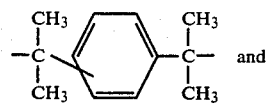 and

R$_1'$ to R$_4'$ are identical or different and denote H, Br or Cl, and at least one R' is Br or Cl, characterized in that said statistical mixtures have a total halogen content of about 3 to 48% by weight and contain about 0–48% by weight of bromine alone, about 0–30% by weight of chlorine alone or bromine and chlorine conjointly in any desired ratios by weight and wherein said statistical mixtures of bisphenols are prepared by a process comprising bringing bisphenols of formula II in the solid form into contact at temperatures between about −20° C. and +80° C., with gaseous chlorine, bromine, or chlorine and bromine, optionally using an inert gas, and subsequently withdrawing the resulting statistical mixture of bisphenols from the further reaction after the desired halogen content has been reached.

6. A composition comprising high-molecular weight, thermoplastic, aromatic polycarbonates containing halogen selected from the group consisting of bromine and chlorine having recurrent but not identical structural units of the following formula III

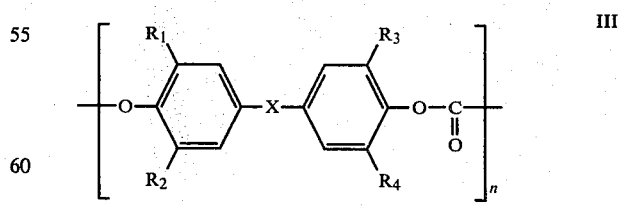

wherein
X denotes C$_1$–C$_9$ alkylene, C$_2$–C$_9$ alkylidene, C$_5$–C$_{15}$ cycloalkylene, C$_5$–C$_{15}$ cycloalkylidene, a single bond,
—O—, —S—, —SO—, —SO$_2$—, —CO— or

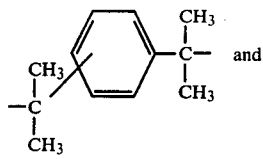

R$_1$ to R$_4$ are identical or different and denote H, Br or Cl, and n is an integer between 20 and 800, wherein said polycarbonates are prepared from statistical mixtures comprising halogen-free bisphenols of the formula II with mono-, di-, tri- and tetra-halogenated bisphenols, wherein the halogen is selected from the group consisting of bromine and chlorine, of the formula I

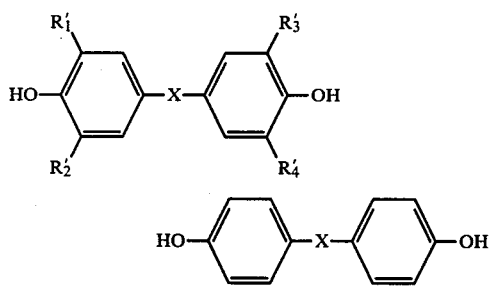

wherein
X denotes C$_1$–C$_9$ alkylene, C$_2$–C$_9$ alkylidene, C$_5$–C$_{15}$ cycloalkylene, C$_5$–C$_{15}$ cycloalkylidene, a single bond,
—O—, —S—, —SO—, —SO$_2$—, —CO— or

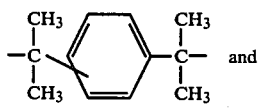

R$_1'$ to R$_4'$ are identical or different and denote H, Br or Cl, and at least one R' is Br or Cl, characterized in that said statistical mixtures have a total halogen content of about 3 to 48% by weight and contain about 0–48% by weight of bromine alone, about 0–30% by weight of chlorine alone or bromine and chlorine conjointly in any desired ratios by weight and wherein said statistical mixtures of bisphenols are prepared by a process comprising suspending bisphenols of formula II in about 2 to 5 times the amount by weight of a halogen-containing hydrocarbon and reacting, at temperatures between about −20° C. and +80° C., with the amounts of bromine, chlorine, or bromine and chlorine required for the desired halogen content in the mixtures of bisphenols.

7. Polycarbonates according to claim 1, wherein the total halogen content is between about 3 and 27% by weight.

8. Polycarbonates according to claim 2, wherein the total halogen content is between about 3 and 27% by weight.

9. Polycarbonates according to claim 3, wherein the total halogen content is between about 3 and 27% by weight.

10. Polycarbonate compositions according to claim 1, wherein up to about 40% by weight of glass fibers are included.

11. Polycarbonate compositions according to claim 2, wherein up to about 40% by weight of glass fibers are included.

12. Polycarbonate compositions according to claim 3, wherein up to about 40% by weight of glass fibers are included.

13. A composition comprising the polycarbonate of claim 1 and a polymer selected from the group consisting of halogen-free, thermoplastic, aromatic polycarbonates and thermoplastic polyesters.

14. A composition comprising the polycarbonate of claim 2 and a polymer selected from the group consisting of halogen-free, thermoplastic, aromatic polycarbonates and thermoplastic polyesters.

15. A composition comprising the polycarbonate of claim 3 and a polymer selected from the group consisting of halogen-free, thermoplastic, aromatic polycarbonates and thermoplastic polyesters.

16. In a process for the preparation of polycarbonates from hydroxyl-bearing compounds, the improvement comprising using statistical mixtures of bisphenols as the hydroxyl-bearing compounds, said statistical mixtures comprising halogen-free bisphenols of the formula II with mono-, di-, tri- and tetra-halogenated bisphenols, wherein the halogen is selected from the group consisting of bromine and chlorine of the formula I

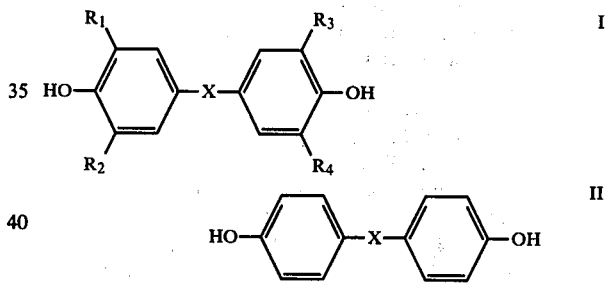

wherein
X denotes C$_1$–C$_9$ alkylene, C$_2$–C$_9$ alkylidene, C$_5$–C$_{15}$ cycloalkylene, C$_5$–C$_{15}$ cycloalkylidene, a single bond, —O—, —S—, —SO—, —SO$_2$—, —CO— or

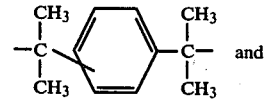

R$_1$ to R$_4$ are identical or different and denote H, Br or Cl, and at least one R is Br or Cl, and wherein the total halogen content of the statistical mixtures is about 3 to 48% by weight and they contain about 0–48% by weight of bromine alone, about 0–30% by weight of chlorine alone or bromine and chlorine conjointly in any desired ratios by weight.

17. In a process for the preparation of polycarbonates from hydroxyl-bearing compounds, the improvement comprising using statistical mixtures of bisphenols as the hydroxyl-bearing compounds, said statistical mixtures comprising halogen-free bisphenols of the formula II with mono-, di-, tri- and tetra- halogenated bisphenols, wherein the halogen is selected from the group consisting of bromine and chlorine, of the formula I

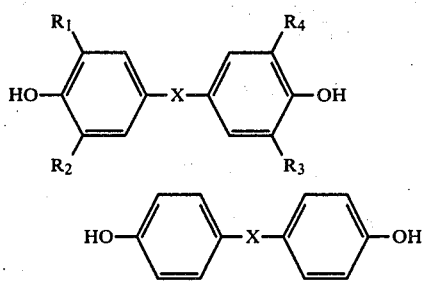

wherein
X denotes $C_1$–$C_9$ akylene, $C_2$–$C_9$ alkylidene, $C_5$–$C_{15}$ cycloalkylene, $C_5$–$C_{15}$ cycloalkylidene, a single bond, —O—, —S—, —SO—, —SO$_2$—, —CO— or

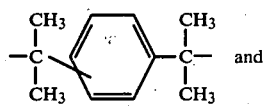

and $R_1$ to $R_4$ are identical or different and denote H, Br or Cl and at least one R is Br or Cl, characterized in that said statistical mixtures have a total halogen content of about 3 to 48% by weight and contain about 0–48% by weight of bromine alone, about 0–30% by weight of chlorine alone or bromine and chlorine conjointly in any desired ratios by weight and wherein said statistical mixtures of bisphenols are prepared by a process comprising bringing bisphenols of formula II in the solid form into contact at temperatures between about −20° C. and +80° C., with gaseous chlorine, bromine, or chlorine and bromine optionally using an inert gas, and subsequently withdrawing the resulting statistical mixture of bisphenols from the further reaction after the desired halogen content has been reached.

18. In a process for the preparation of polycarbonates from hydroxyl-bearing compounds, the improvement comprising using statistical mixtures of bisphenols as the hydroxyl-bearing compounds, said statistical mixtures comprising halogen-free bisphenols of the formula II with mono-, di-, tri- and tetra-halogenated bisphenols, wherein the halogen is selected from the group consisting of bromine and chlorine, of the formula I

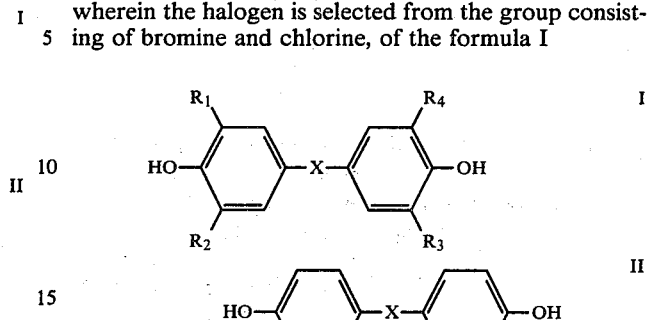

wherein
X denotes $C_1$–$C_9$ alkylene, $C_2$–$C_9$ alkylidene, $C_5$–$C_{15}$ cycloalkylene, $C_5$–$C_{15}$ cycloalkylidene, a single bond, —O—, —S—, —SO—, —SO$_2$—, —CO— or

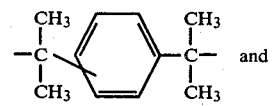

and $R_1$ to $R_4$ are identical or different and denote H, Br or Cl and at least one R is Br or Cl, characterized in that said statistical mixtures have a total halogen content of about 3 to 48% by weight and contain about 0–48% by weight of bromine alone, about 0–30% by weight of chlorine alone or bromine and chlorine conjointly in any desired ratios by weight and wherein said statistical mixtures of bisphenols are prepared by a process comprising suspending the bisphenols of formula II in about 2 to 5 times the amount by weight of a halogen-containing hydrocarbon and reacting, at temperatures between about −20° C. and +80° C., with the amounts of bromine, chlorine, or bromine and chlorine required for the desired halogen content in the mixture of bisphenols.

* * * * *